US012758777B2

(12) United States Patent
Min et al.

(10) Patent No.: US 12,758,777 B2
(45) Date of Patent: Oct. 13, 2026

(54) NEURAL STIMULATION DEVICE, NEURAL STIMULATION SYSTEM, AND CONTROL METHOD

(71) Applicant: Amygdala Neuro Technologies (ShenZhen) Co., Ltd., Shenzhen (CN)

(72) Inventors: Xiaoyi Min, Shenzhen (CN); Jianjiang Yao, Shenzhen (CN); Jianfeng Zhang, Shenzhen (CN)

(73) Assignee: Amygdala Neuro Technologies (ShenZhen) Co., Ltd., Shenzhen (CN)

( * ) Notice: Subject to any disclaimer, the term of this patent is extended or adjusted under 35 U.S.C. 154(b) by 283 days.

(21) Appl. No.: 18/440,937

(22) Filed: Feb. 13, 2024

(65) Prior Publication Data

US 2024/0181259 A1 Jun. 6, 2024

Related U.S. Application Data

(63) Continuation-in-part of application No. PCT/CN2022/113086, filed on Aug. 17, 2022.

(30) Foreign Application Priority Data

Aug. 18, 2021 (CN) ........................ 202110950387.7

(51) Int. Cl.
*A61N 1/36* (2006.01)

(52) U.S. Cl.
CPC ..... *A61N 1/36139* (2013.01); *A61N 1/36062* (2017.08); *A61N 1/36167* (2013.01)

(58) Field of Classification Search
CPC ........... A61N 1/36139; A61N 1/36062; A61N 1/36167; A61N 1/36071; A61N 1/36175;
(Continued)

(56) References Cited

U.S. PATENT DOCUMENTS 5,792,212 A * 8/1998 Weijand .................. A61B 5/24
600/554
6,185,454 B1 * 2/2001 Thompson ............ A61N 1/378
607/2

(Continued)

FOREIGN PATENT DOCUMENTS

CN 104225790 A 12/2014
CN 106963377 A 7/2017

(Continued)

OTHER PUBLICATIONS

Sung-Hao Wang et al., "Design of a Bone-Guided Cochlear Implant Microsystem With Monopolar Biphasic Multiple Stimulations and Evoked Compound Action Potential Acquisition and Its In Vivo Verification", IEEE Journal of Solid-State Circuits, vol. 56, No. 10, Jun. 21, 2021, 15 pgs.

(Continued)

*Primary Examiner* — Paula J Stice
(74) *Attorney, Agent, or Firm* — USCH Law, PC

(57) ABSTRACT

A neural stimulation device is provided, including: a neural stimulation controller, a pulse generator, and an evoked compound action potential (ECAP) sensor. The neural stimulation controller is configured to: instruct the ECAP sensor to turn on while instructing the pulse generator to generate the pulse, instruct the ECAP sensor to sense the evoked compound action potential after instructing the pulse generator to generate the stimulation pulse and elapsing of a sensing delay time, and instruct the ECAP sensor to turn off after instructing the ECAP sensor to sense the evoked compound action potential and elapsing of an ECAP window time. The sensing delay time is the greater of a total duration of the pulse and a predetermined time.

18 Claims, 5 Drawing Sheets

(58) Field of Classification Search
CPC .............. A61N 1/36128; A61N 1/3605; A61N 1/36132; A61N 1/36135; A61N 1/0551; A61N 1/025
See application file for complete search history.

(56) References Cited

U.S. PATENT DOCUMENTS

| | | | |
|---|---|---|---|
| 2014/0275926 A1 | 9/2014 | Scott et al. | |
| 2018/0126169 A1 | 5/2018 | Hou et al. | |
| 2019/0298992 A1* | 10/2019 | Zhang | A61N 1/0553 |
| 2019/0366094 A1* | 12/2019 | Esteller | A61N 1/36135 |
| 2021/0121698 A1* | 4/2021 | Dinsmoor | A61N 1/36192 |
| 2021/0121699 A1 | 4/2021 | Dinsmoor et al. | |
| 2021/0121700 A1 | 4/2021 | Dinsmoor et al. | |

FOREIGN PATENT DOCUMENTS

| | | | |
|---|---|---|---|
| CN | 109561849 | A | 4/2019 |
| CN | 110072590 | A | 7/2019 |
| CN | 112351813 | A | 2/2021 |
| CN | 112351814 | A | 2/2021 |
| CN | 113908436 | A | 1/2022 |
| WO | 2020082129 | A1 | 4/2020 |

OTHER PUBLICATIONS

Amygdala Neuro Technologies (ShenZhen) Co., Ltd., Extended European Search Report, EP 22857855.5, Oct. 21, 2024, 10 pgs.
Amygdala Neuro Technologies (ShenZhen) Co., Ltd., International Search Report with English translation, PCT/CN2022/113086, Nov. 2, 2022, 7 pgs.

* cited by examiner

NEURAL STIMULATION DEVICE, NEURAL STIMULATION SYSTEM, AND CONTROL METHOD

CROSS-REFERENCE TO RELATED APPLICATION

The present application is a continuation in part of PCT Patent Application No. PCT/CN2022/113086, filed Aug. 17, 2022, which claims priority to Chinese Patent Application No. 202110950387.7, filed Aug. 18, 2021, each of which is incorporated by reference herein in its entirety.

TECHNICAL FIELD

Embodiments of the present disclosure relate in general to the field of medical devices, and in particular to a neural stimulation device, a neural stimulation system, and a control method.

BACKGROUND

With the progress and development of science and technology, the technology of controlling and treating diseases by sending neural stimulation has gradually matured. A so-called closed-loop function of neural stimulation can obtain the response of an organ to the stimulation, and thus adjusts the pulse to achieve better therapeutic effects. The evoked compound action potential (ECAP) is an external expression of the response of fiber populations to electrical stimulation. Clinical studies have demonstrated new scientific evidence supporting the implementation of closed-loop spinal cord stimulation (SCS) systems for the treatment of chronic pain based on feedback control of ECAP. ECAP sensing can be performed during SCS, and a relationship between pulsatile stimulation, electrophysiologic response, and neuromodulation is obtained based on the sensing results. Therefore, major SCS manufacturers add this new feature into next-generation SCS systems to realize the closed-loop function in SCS. Specifically, response of the spinal cord to stimulation is first sensed, i.e., a complex action potential is stimulated, and then a pulse duration, pulse intensity and pulse generation period are adjusted based on the sensed ECAP results to improve activation within a patient's therapeutic window, and to maintain a long-term therapeutic effect of the stimulation.

Existing neural stimulation devices generally have a plurality of stimulation electrodes (with more than 8 to 16 contacts), and the power consumption of the neural stimulation device has been relatively high. In order to realize pulse adjustment based on the sensed ECAP results, it is required to add an ECAP sensing function module to the neural stimulation device, and the added ECAP sensing function module will further increase the power consumption of the entire device. Reducing the power consumption is necessary to reduce a size of an implantable pulse generator (IPG) and to extend a charging interval of batteries of the device. However, additional high-power consumption caused by the added ECAP sensing function module is a huge problem in reducing the size of the IPG and extending the charging interval of the device.

SUMMARY

Embodiments of the present disclosure are intended to provide a neural stimulation device. After the pulse is generated, the neural stimulation device senses the ECAP at regular start times and with regular durations within a specific time period after a sensing delay time. By selectively turning on the ECAP sensor for sensing the ECAP, the power consumption of the ECAP sensor is reduced and overall power consumption of the neural stimulation device is reduced as much as possible, which lays a good foundation for reducing the size of the neural stimulation device and extending the charging interval of the device.

Some embodiments of the present disclosure provide a neural stimulation device including: a neural stimulation controller, a pulse generator, and a ECAP sensor; where the neural stimulation controller is configured to: instruct the ECAP sensor to turn on while instructing the pulse generator to generate the pulse; instruct the ECAP sensor to sense the evoked compound action potential after instructing the pulse generator to generate the pulse and elapsing of a sensing delay time; and instruct the ECAP sensor to turn off after instructing the ECAP sensor to sense the evoked compound action potential and elapsing of an evoked compound action potential, ECAP, window time; where the sensing delay time is the greater of a total duration of the pulse and a predetermined time.

Some embodiments of the present disclosure further provide a neural stimulation system including a neural stimulation device and an electrode lead electrically connected to the neural stimulation device; where the neural stimulation device includes a neural stimulation controller, a pulse generator, and an evoked compound action potential (ECAP) sensor; and where the neural stimulation controller is configured to: instruct the ECAP sensor to turn on while instructing the pulse generator to generate the pulse; instruct the ECAP sensor to sense an evoked compound action potential after instructing the pulse generator to generate the pulse and elapsing of a sensing delay time; and instruct the ECAP sensor to turn off after instructing the ECAP sensor to sense the evoked compound action potential and elapsing of an ECAP window time; where the sensing delay time is the greater of a total duration of the pulse and a predetermined time.

Some embodiments of the present disclosure further provide a control method applied at a neural stimulation device; and where the neural stimulation device includes a neural stimulation controller, a pulse generator, and an evoked compound action potential (ECAP) sensor; and where the neural stimulation controller is configured to: instruct the ECAP sensor to turn on while instructing the pulse generator to generate the pulse; instruct the ECAP sensor to sense an evoked compound action potential after instructing the pulse generator to generate the pulse and elapsing of a sensing delay time; and instruct the ECAP sensor to turn off after instructing the ECAP sensor to sense the evoked compound action potential and elapsing of an ECAP window time; where the sensing delay time is the greater of a total duration of the pulse and a predetermined time.

In the neural stimulation device provided in the present disclosure, the neural stimulation controller instructs the ECAP sensor to turn on while instructing the pulse generator to generate the pulse, instructs the ECAP sensor to sense an evoked compound action potential after elapsing of the sensing delay time, and controls the ECAP sensor to turn off after sensing the evoked compound action potential and elapsing of the ECAP window time. Therefore, the neural stimulation device in the present disclosure pre-sets the duration of each phase of the evoked compound action potential sensing process by providing the sensing delay time from the generation of the pulse to the start of the sensing, and the ECAP window time of the sensing duration of the evoked compound action potential, etc., so as to control the sensing of the evoked compound action potential to be started at regular times and last for regular durations within the specified time period, which avoids the ECAP sensor for sensing the evoked compound action potential to turn on for a long period of time while ensuring the accuracy of a sensing result of the evoked compound action potential, thereby reducing the overall power consumption of the neural stimulation device as much as possible, and laying a good foundation for reducing a design size of the neural stimulation device and extending the charging interval of the neural stimulation device.

BRIEF DESCRIPTION OF THE DRAWINGS

One or more embodiments are illustrated exemplarily with reference to the accompanying drawings, and these exemplary descriptions do not constitute a limitation on the embodiments. Elements having the same reference numeral in the accompanying drawings indicate similar elements, and the figures in the accompanying drawings do not constitute a scale limitation, unless otherwise stated.

DETAILED DESCRIPTION OF THE EMBODIMENTS

Figure 1:
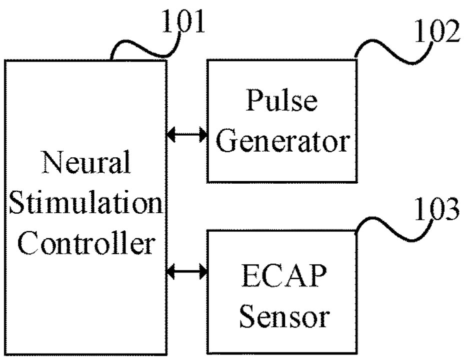
FIG. 1 is a schematic structural diagram of a neural stimulation device according to an embodiment of the present disclosure.

As is seen from the Background, existing neural stimulation devices having a plurality of stimulation electrodes (e.g. with more than 8 to 16 contacts), and the power consumption of the neural stimulation device has been relatively high. In order to realize pulse adjustment based on ECAP sensing results, an ECAP sensing function module is added to the neural stimulation device, which further increases the overall power consumption of the neural stimulation device, thereby causing problems in the size reduction and extension of the charging interval of the neural stimulation device. Therefore, how to provide a neural stimulation device capable of obtaining ECAP sensing results for pulse adjustment with low power consumption is an urgent problem to be solved.

In order to solve the above problem, embodiments of the present disclosure provide a neural stimulation device including a neural stimulation controller, a pulse generator, and a ECAP sensor. The pulse generator is configured to generate a pulse according to an instruction from the neural stimulation controller, the ECAP sensor is configured to sense an evoked compound action potential according to an instruction from the neural stimulation controller, and the neural stimulation controller is configured to instruct the ECAP sensor to turn on while instructing the pulse generator to generate the pulse. The neural stimulation controller instructs the ECAP sensor to sense the evoked compound action potential after instructing the pulse generator to generate the pulse and elapsing of a sensing delay time. The neural stimulation controller instructs the ECAP sensor to turn off after instructing the ECAP sensor to sense the evoked compound action potential and elapsing of an ECAP window time. The sensing delay time is the greater of a total duration of the pulse and a predetermined time.

In the neural stimulation device provided in embodiments of the present disclosure, the neural stimulation controller instructs the ECAP sensor for sensing the evoked compound action potential to turn on while instructing the pulse generator to generate the pulse, instructs the ECAP sensor to sense the evoked compound action potential after the elapsing of the sensing delay time, and instructs the ECAP sensor to turn off after the elapsing of the ECAP window time. Thus, the neural stimulation device provided in the present disclosure pre-sets the duration of each phase of the evoked compound action potential sensing process by providing the sensing delay time from the generation of the pulse to the start of the sensing, and the ECAP window time of the sensing duration of the evoked compound action potential, etc., so as to control the sensing of the evoked compound action potential to be started at regular times and last for regular durations within the specified time period, which avoids the ECAP sensor for sensing the evoked compound action potential to turn on for a long period of time while ensuring the accuracy of a sensing result of the evoked compound action potential, thereby reducing the overall power consumption of the neural stimulation device as much as possible, and laying a good foundation for reducing a design size of the neural stimulation device and extending the charging interval of the neural stimulation device.

In order to make the objectives, technical solutions and advantages of the embodiments of the present disclosure clearer, the embodiments of the present disclosure will be described in detail below with reference to the accompanying drawings. However, those of ordinary skill in the art may understand that in the embodiments of the present disclosure, many technical details are set forth in order to make the reader better understand the present disclosure. However, the technical solutions set forth in the present disclosure may be implemented even without these technical details and various changes and modifications based on the following embodiments. The division of the following various embodiments is for convenience of description, which should not constitute any limitation on the specific implementations of the present disclosure, and various embodiments may be mutually referenced on the premise of no contradiction.

The implementation details of the neural stimulation device described in the present disclosure are specifically described below with reference to specific embodiments, and the following content merely describes implementation details for case of understanding, and is not necessary for implementation of the technical solution in the present disclosure.

A first aspect of the embodiments in the present disclosure provides a neural stimulation device, which is able to be applied to various neural stimulation usage scenarios, such as spinal cord stimulation (SCS), dorsal root ganglion stimulation (DRG), sympathetic nerve stimulation (SNS), vagus nerve stimulation (VNS), deep brain stimulation (DBS), and the like. This embodiment illustrates the application of the neural stimulation device in the scenario of the spinal cord stimulation.

As shown in FIG. 1, an embodiment of the present disclosure provides a neural stimulation device including the following components.

A neural stimulation controller 101 is configured to instruct an ECAP sensor to turn on while instructing a pulse generator to generate a pulse. The neural stimulation controller instructs the ECAP sensor to sense an evoked compound action potential (ECAP) after instructing the pulse generator to generate the stimulation pulse and elapsing of a sensing delay time, and the neural stimulation controller instructs the ECAP sensor to turn off after instructing the ECAP sensor to sense the evoked compound action potential and elapsing of an ECAP window time. The sensing delay time is the greater of a total duration of the pulse and a predetermined time.

A pulse generator 102 is configured to generate a pulse according to an instruction from the neural stimulation controller.

A ECAP sensor 103 is configured to sense the evoked compound action potential according to an instruction from the neural stimulation controller.

The selection of the neural stimulation controller in the actual application has a plurality of options, including any one or any combination of a logic circuit, a micro controller unit (MCU), a central processing unit (CPU), a microprocessor, a programmable logic controller (PLC), a field programmable gate array (FPGA), a programmable array logic (PAL), a generic array logic (GAL), and a complex programmable logic device (CPLD), and a specific selection of the neural stimulation controller in this embodiment is not limited.

The selection of the pulse generator in the actual application has a plurality of options, including a pulse generation circuit, e.g., a boosting circuit including a boosting component and related circuits, the boosting component may be a boost IC chip, a charge pump (switched capacitor converter) or an inductive DC-DC converter, and a specific selection of the pulse generator in this embodiment is not limited.

The selection of the ECAP sensor in the actual application has a plurality of options, including a sensing circuit. The sensing circuit includes a filter and related circuits, an amplifier and related circuits, and analog-to-digital conversion circuits. In some embodiments, the sensing circuit further includes a comparator to determine whether a valid signal is perceived, and a specific selection of the ECAP sensor in this embodiment is not limited.

Figure 2:
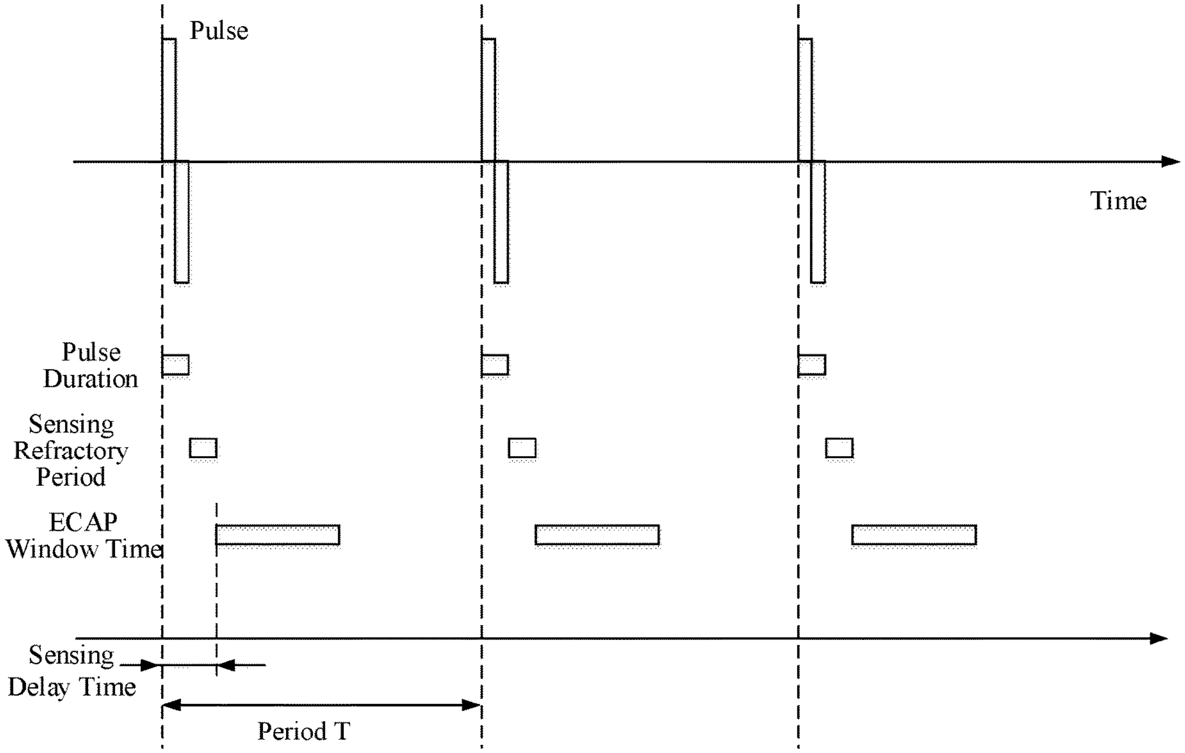
FIG. 2 is a timing diagram of operating of a spinal cord stimulation device according to an embodiment of the present disclosure.

Specifically, the spinal cord stimulation device may, before being implanted into a user's body, predetermine or pre-store pulses, and sense various relevant parameters, such as pulse frequency, pulse intensity, pulse generation period, pulse duration, sensing duration of the evoked compound action potential (i.e., the ECAP window time), etc. As shown in FIG. 2, the neural stimulation controller obtains a pulse generation period T according to a reciprocal of an initial pulse generation frequency f and sends a pulse generation instruction to the pulse generator, and the pulse generator generates a specified pulse according to the pulse generation instruction. Then, after elapsing of a period T', the neural stimulation controller sends a new pulse generation instruction to the pulse generator. For example, a period of pulse generation is generally greater than 6.67 ms (a corresponding pulse generation frequency is 150 Hz), and a period of initial pulse generation in this example is 20 ms (a corresponding pulse generation frequency is 50 Hz). In a closed-loop system, a current period T may be the same as or different from a next period T'. The neural stimulation controller sends a turn-on instruction to the ECAP sensor while instructing the pulse generator to generate the pulse, and the ECAP sensor is triggered to turn on. After instructing the pulse generator to generate the pulse and elapsing of the sensing delay time, the neural stimulation controller sends a sensing instruction to the ECAP sensor, and the ECAP sensor senses the evoked compound action potential according to the sensing instruction. After instructing the ECAP sensor to sense the evoked compound action potential and elapsing of the ECAP window time, the neural stimulation controller sends a turn-off instruction to the ECAP sensor, and the ECAP sensor enters a turn-off state according to the turn-off instruction.

The sensing delay time is the greater of the total duration of the pulse and the predetermined time. The predetermined time can be a parameter t_sw stored in the neural stimulation controller of the neural stimulation device. The parameter t_sw is able to be adjusted by means such as programming and is a parameter related to time as well as related to hardware of the neural stimulation device, and t_sw is configured for identifying a duration of status switching of the sensor in the neural stimulation device. The total duration of the pulse includes a pulse duration and a sensing refractory period. The pulse duration includes a primary stimulation pulse time, a recovery/charge balance pulse time, and an interval time between the primary stimulation pulse time and the recovery/charge balance pulse time. The sensing refractory period is set to avoid circuit discharge and hardware oscillation from affecting the sensing, and the sensing refractory period is related to the hardware of the neural stimulation device. In order to meet dual requirements of sensing precision and reducing power consumption as much as possible, the sensing delay time for sensing the evoked compound action potential needs to consider both the total duration of the pulse and the predetermined time. Compared with a neural stimulation device in which the ECAP sensor is always sensing, the power consumption of the neural stimulation device in this embodiment when applied to the spinal cord stimulation may be as low as a quarter of the power consumption of the former (by generating the pulse at a generating frequency of 50 Hz).

After instructing the ECAP sensor to turn on, the neural stimulation controller determines that a time for instructing the ECAP sensor to sense the evoked compound action potential, that is, the sensing delay time. In this embodiment, if the predetermined parameter t_sw (status switching time of the ECAP sensor) is greater than or equal to the total duration of the pulse composed of the pulse duration and a sensing refractory period, the neural stimulation controller directly takes t_sw as the sensing delay time. If the parameter t_sw is less than the total duration of the pulse composed of the pulse duration and the sensing refractory period, the neural stimulation controller takes the total duration of the pulse as the sensing delay time. By setting the sensing delay time as the greater of the total duration of the pulse and the status switching time of the ECAP sensor, it is avoided that the evoked compound action potential is sensed in the period during which the evoked compound action potential cannot be effectively sensed, and the power consumption of the spinal cord stimulation device is reduced as much as possible.

Figure 8:
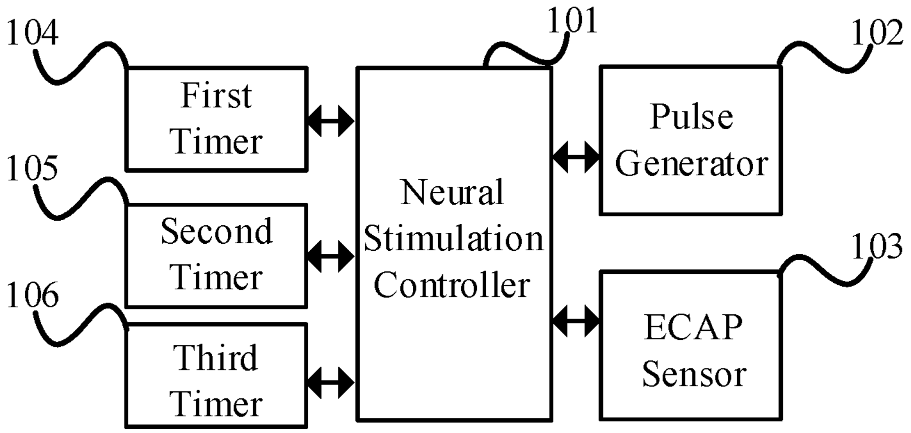
FIG. 8 is still another schematic structural diagram of a neural stimulation device according to an embodiment of the present disclosure.

The neural stimulation device further includes at least one timer. The timer has a timing mode for making a specific action happen on time. In addition, the timer may further have other functions, such as a time keeping mode for recording a real time when a specific action or signal occurs. In some embodiments, as shown in FIG. 8, the neural stimulation device includes a first timer 104, a second timer 105, and a third timer 106. The first timer is configured to be in a first timing mode having a first timing duration, and the first timing duration is a duration of a pulse generation period. When the pulse generation period expires and the first timer overflows, the neural stimulation controller instructs the ECAP sensor to turn on. For example, the neural stimulation controller maintains a sleep state all the time, so as to further reduce power consumption. When the first timer overflows, the neural stimulation controller is woken up in an interrupted manner. When the neural stimulation controller instructs the ECAP sensor to turn on, the second timer is configured to be in a second timing mode having a second timing duration, and the second timing duration is a duration of the sensing delay time. When the sensing delay time expires and the second timer overflows, the neural stimulation controller instructs the ECAP sensor to sense the evoked compound action potential. When the neural stimulation controller instructs the ECAP sensor to sense the evoked compound action potential, the third timer is configured to be in a third timing mode having a third timing duration, and the third timing duration is a duration of the ECAP window time. When the ECAP window time expires and the third timer overflows, the neural stimulation controller instructs the ECAP sensor to turn off.

During operation of the neural stimulation device, the neural stimulation controller resets the first timer to enter the timing mode again when the pulse generation period expires and the first timer overflows. At this time, the neural stimulation controller sends the pulse generation instruction to the pulse generator to control the pulse generator to generate a new pulse, and sends the turn-on instruction to the ECAP sensor to control the ECAP sensor to turn on. Meanwhile, the neural stimulation controller turns on the second timer, the second timer is also configured to be in a second timing mode having a second timing duration, and the second timing duration is the duration of the sensing delay time. When the second timer overflows, the neural stimulation controller determines that the sensing delay time has elapsed after instructing the pulse generator to generate the pulse, and the sensing (ECAP sensing) of the evoked compound action potential needs to be initiated, so the neural stimulation controller sends a sensing instruction to the ECAP sensor and turns off the second timer. Meanwhile, the neural stimulation controller turns on the third timer. The third timer is also configured to be in a third timing mode having a third timing duration, and the third timing duration is the duration of the ECAP window time. When the third timer overflows, the neural stimulation controller determines that the sensing duration of the evoked compound action potential has reached the duration of the predetermined ECAP window time, then sends the turn-off instruction, and the third timer and the ECAP sensor are turned off to enter the turn-off state.

In addition, the neural stimulation device further includes a sixth timer configured to realize pulse stopping. Similar to other timers, the sixth timer has a sixth timing mode. When the first timer overflows, the neural stimulation controller turns on the sixth timer, and a sixth timing duration is the pulse duration. When the pulse duration expires and the sixth timer overflows, the neural stimulation controller sends a pulse stopping instruction to the pulse generator, and the pulse generator stops generating the pulse according to the instruction. The neural stimulation controller also turns off the sixth timer accordingly.

The selection of the timer in the actual application has a plurality of options, including a circuit having a timing function, which is generated by a MCU or digital circuit controller with a crystal oscillator circuit or phase-locked loop (PLL) circuit as a reference clock source, and a specific selection of the timer in this embodiment is not limited.

In another example, the neural stimulation device may also be applied to dorsal root ganglion stimulation, sympathetic nerve stimulation, vagus nerve stimulation, or deep brain stimulation. When the neural stimulation device is used in different scenarios, the total duration of the pulse is adjusted according to specific needs, and the neural stimulation controller determines a new sensing delay time according to a total duration of a new pulse and the status switching time. In this way, precise sensing of the evoked compound action potential is ensured as much as possible while reducing the overall power consumption of the neural stimulation device, which is conducive to adjusting pulse-related parameters according to the sensing result.

The neural stimulation controller is further configured to determine whether the evoked compound action potential needs to be sensed before instructing the ECAP sensor to turn on. The neural stimulation controller instructs the ECAP sensor to turn on in response to that the evoked compound action potential needs to be sensed, and then instructs the ECAP sensor to sense the evoked compound action potential. In practical application, in order to reduce power consumption, the sensing of the evoked compound action potential may not be performed at each pulse generation period. A cycle period consisting of a plurality of pulse generation periods can be set, the evoked compound action potential is sensed in some of the pulse generation periods in the cycle period, and the evoked compound action potential is no longer sensed within other periods in the cycle period. In addition, when an accident occurs, for example, when the electric quantity is lower than a threshold, or when the ECAP sensor goes wrong, the neural stimulation controller may also determine that the evoked compound action potential is no longer sensed.

Figure 3:
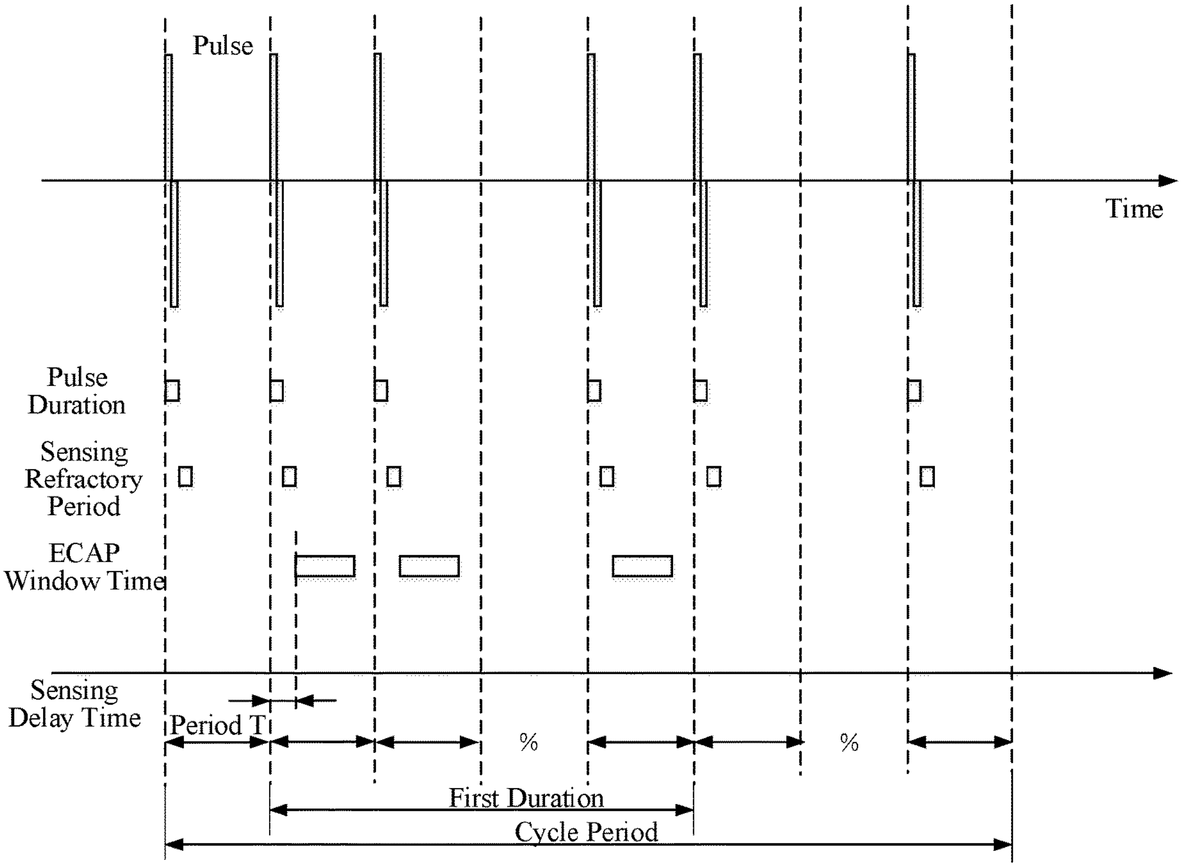
FIG. 3 is another timing diagram of operating of a spinal cord stimulation device according to an embodiment of the present disclosure.

In one example, the neural stimulation controller determining whether the evoked compound action potential needs to be sensed includes: obtaining an accumulated duration of pulse generation periods in which the evoked compound action potential has been sensed in a current cycle period, and determining that the evoked compound action potential needs to be sensed in response to the accumulated duration being less than a first duration that is predetermined. The current cycle period includes at least two pulse generation periods. As shown in FIG. 3, in the neural stimulation controller of the neural stimulation device for spinal cord stimulation, cycle periods for generating the pulse and the accumulated duration of pulse generation periods for sensing the evoked compound action potential in each cycle period, i.e., the first duration, are predetermined. Herein, the cycle period and the first duration may be set according to a physical condition of the user, for example, the cycle period is 1 minute, 3 minutes, or 5 minutes. After the current cycle period starts, the neural stimulation controller counts the accumulated duration of the pulse generation periods in which the ECAP sensor has sensed the evoked compound action potential. When the accumulated duration of the pulse generation periods in which the evoked compound action potential has been sensed in the current cycle period does not reach the first duration, it is indicated that the evoked compound action potential still needs to be sensed, and the neural stimulation controller instructs the ECAP sensor to turn on and sends a control instruction to the ECAP sensor after the elapsing of the sensing delay time to instructs the ECAP sensor to sense the evoked compound action potential during the ECAP window time. After the accumulated duration reaches the first duration, it is indicated that the evoked compound action potential does not need to be sensed in subsequent pulse generation periods any more, and the neural stimulation controller no longer instructs the ECAP sensor to turn on while instructing the pulse generator to generate the pulse until entering a next cycle period.

Figure 9:
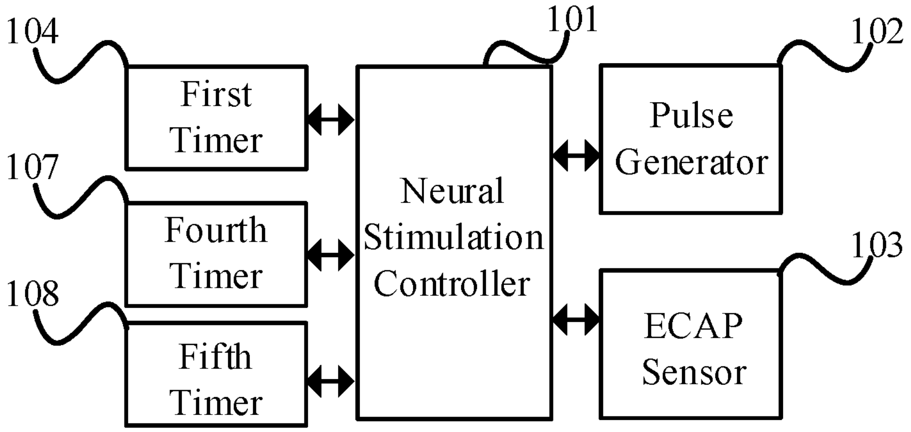
FIG. 9 is yet another schematic structural diagram of a neural stimulation device according to an embodiment of the present disclosure.

More specifically, as shown in FIG. 9, the neural stimulation device includes a first timer 104, a fourth timer 107, and a fifth timer 108. When the cycle period starts, the neural stimulation controller instructs the first timer and the fourth timer to turn on, the first timer is configured to be in a first timing mode having a first timing duration, and the first timing duration is the duration of the pulse generation period. The fourth timer is configured to be in a fourth timing mode having a fourth timing duration, and the fourth timing duration is a duration of the cycle period. When the cycle period starts or after the cycle period starts, the neural stimulation controller instructs the fifth timer to turn on, and the fifth timer is configured to be in a fifth timing mode having a fifth timing duration, and the fifth timing duration is the first duration. When the fourth timer and the fifth timer do not overflow and the first timer overflows, the neural stimulation controller determines that the evoked compound action potential needs to be sensed in this pulse generation period, instructs the ECAP sensor to turn on while instructing the pulse generator to generate the pulse, and then instructs the ECAP sensor to sense the evoked compound action potential. At the same time, the neural stimulation controller instructs the first timer to be reset. When the fifth timer overflows, sufficient information of the evoked compound action potential has been obtained in the current cycle period, and the neural stimulation controller instructs the fifth timer to turn off. When the fourth timer overflows, the current cycle period has expired, the next cycle period starts, and the neural stimulation controller instructs the fourth timer to be reset. In an alternative embodiment, the cycle period is described with the number of pulse generation periods rather than the duration, and the pulse generation periods in which the ECAP sensor has sensed the evoked compound action potential are also described in the number rather than the duration. In this case, a counter is used to record related numbers. For example, in a cycle period, a first counter is incremented by one when the first timer overflows, and the second counter incremented by one when a pulse generation period in which the ECAP sensor senses the evoked compound action potential is generated. This embodiment is a deformation of the above embodiments, which also fall within the protection scope of the present disclosure.

In another alternative embodiment, statistics about the cycle period is performed by means of the duration. In a case where the first duration and the cycle period synchronously start/expire, it is achieved that the evoked compound action potential is sensed in some of the pulse generation periods in one cycle period and is not sensed in remaining pulse generation periods in the cycle period by means of a parameter (i.e., a blank sensing duration) of an accumulated duration of pulse generation periods in which the evoked compound action potential is not sensed among the pulse generation periods as well as a parameter (i.e., the first duration) of the accumulated duration of pulse generation periods in which the evoked compound action potential is allowed to be sensed among the pulse generation periods. At this time, a sum of the blank sensing duration and the first duration is one cycle period. For example, at the beginning of one cycle period, the fourth timer is configured to be in a fourth timing mode and starts timing, and a fourth timing duration is the blank sensing duration. Before the fourth timer overflows, the neural stimulation controller controls the third timer and the ECAP sensor to be in a turn-off state all the time. When the fourth timer overflows, the neural stimulation controller instructs the fifth timer to turn on, and configures the fifth timer to be in a fifth timing mode, and a fifth timing duration of the fifth timer is the first duration. When the fifth timer does not overflow, in each pulse generation period, the neural stimulation controller sends a turn-on instruction to the ECAP sensor while sending the pulse generation instruction to the pulse generator, instructs the ECAP sensor to sense the evoked compound action potential after the elapsing of the sensing delay time. When the fifth timer overflows, the current cycle period expires, and the neural stimulation controller instructs the fourth timer to turn on again and instructs the fifth timer to turn off to enter a next cycle period. The blank sensing duration and the first duration may be set according to actual situations.

For example, when the first duration is set in a case where the neural stimulation device is applied to the spinal cord stimulation, a specific value of the first duration can be considered according to the respiratory rhythm of the user, and a specific value of the blank sensing duration can be set according to factors such as living habits and physical quality of the user, which are not limited in this embodiment. The overall power consumption of the neural stimulation device is further reduced by sensing the evoked compound action potential in some of the pulse generation periods in one cycle and not sensing the evoked compound action potential in the remaining pulse generation periods.

In another example, the accumulated duration of pulse generation periods in which the evoked compound action potential is sensed by the neural stimulation device, i.e., the first duration, is determined according to vital sign parameters of the user, and the vital sign parameters include any one or any combination of a respiration beat, a heartbeat rate, and a blood pressure value. The first duration for sensing the evoked compound action potential by the neural stimulation device is set based on the vital sign parameters of the user, and the overall energy consumption of the neural stimulation device is reduced as much as possible while ensuring the sensing effectiveness.

Figure 7:
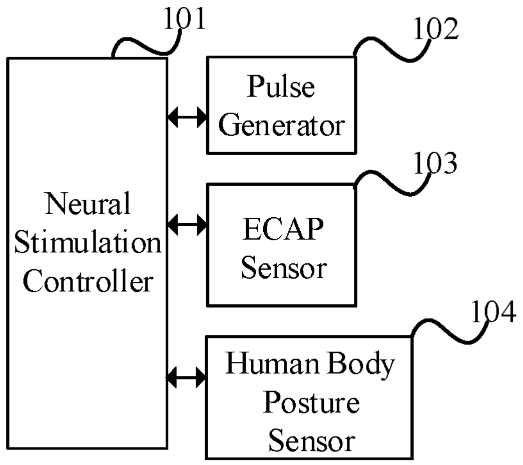
FIG. 7 is another schematic structural diagram of a neural stimulation device according to an embodiment of the present disclosure.

As shown in FIG. 7, the neural stimulation device further includes a human body posture sensor 104. The human body posture sensor is configured to sense a real-time posture of a human body. The neural stimulation controller is further configured to communicate with the human body posture sensor to obtain a human body posture, restart a new cycle period in response to detecting that the human body posture changes within the current cycle period, and reset the accumulated duration to zero. For example, the neural stimulation device for spinal cord stimulation enters a working state after setting parameters such as a cycle period, a first duration, and a pulse generation period. The neural stimulation controller obtains the accumulated duration of pulse generation periods in which the evoked compound action potential is sensed in the current cycle period by means of the timer, and obtains real-time posture data of the user by means of a posture sensor to detect whether the posture of the user changes. In one cycle period, if the accumulated duration has reached the first duration, the neural stimulation controller no longer sends a turn-on instruction to the ECAP sensor within the new pulse generation period, and the ECAP sensor maintains the turn-off state. In this case, if the neural stimulation controller detects that the posture of the user changes by means of the human body posture sensor, the neural stimulation controller interrupts the current cycle period, restarts from a next pulse generation period as the new cycle period, resets the accumulated duration of pulse generation periods in which the evoked compound action potential has been sensed in the current cycle period as well as the duration that the current cycle period has elapsed to zero, and controls the fourth timer to restart a new timing. At the beginning of a certain pulse generation period of the new cycle period, the neural stimulation controller sends the turn-on instruction to the ECAP sensor while instructing the pulse generator to generate the pulse, sends a turn-on instruction to the fifth timer, and instructing, after elapsing of the sensing delay time, the ECAP sensor to sense the evoked compound action potential after the posture of the user changes. If the accumulated duration is still less than the first duration, i.e., the evoked compound action potential is still sensed in the current pulse generation period, the processing is similar to the above. That is, after this pulse generation period is completed, the neural stimulation controller interrupts the current cycle period, restarts from the next pulse generation period as the new cycle period, resets the accumulated duration of pulse generation periods in which the evoked compound action potential has been sensed in the current cycle period as well as the duration that the current cycle period has elapsed to zero, and controls the fourth timer to restart a new timing. The posture sensor is used for monitoring posture change of the user, and the current cycle period is interrupted in time to restart the new cycle period. The evoked compound action potential after the change of the user posture is sensed in order to obtain the user' reaction to the pulse after the posture change, which facilitates subsequent adjustment of the pulse according to the sensing result, thereby avoiding the user's uncomfortable reaction to the pulse after the posture changes.

The selection of the human body posture sensor in the actual application has a plurality of options, including any one or any combination of a position sensor, attitude sensor, displacement sensor, and acceleration sensor as well as related circuits, and a specific selection of the human body posture sensor in this embodiment is not limited.

The neural stimulation controller is further configured to update parameters of the pulse according to the sensed information of the evoked compound action potential, and send an updated pulse generation instruction to the pulse generator in a next pulse generation period to instruct the pulse generator to adjust subsequent pulses according to the updated pulse generation instruction. For example, in the neural stimulation controller of the neural stimulation device applied to spinal cord stimulation, one or more of the parameters such as the pulse duration, the pulse intensity, the pulse frequency, the pulse generation period and the like are adaptively adjusted according to the sensing result of the ECAP sensor for sensing the evoked compound action potential to determine a more appropriate pulse, and then the neural stimulation controller sends the updated pulse generation instruction to the pulse generator in the next pulse generation period to instruct the pulse generator to generate the pulse according to the updated pulse generation instruction. By adjusting the parameters of the pulse according to the sensing result of the evoked compound action potential, it is ensured that the user can have an effective treatment effect as long as possible under the action of the pulse.

In addition, the neural stimulation controller may send the updated pulse generation instruction to the pulse generator according to the sensing result of the ECAP sensor at the beginning of any pulse generation period, and may also adjust the pulse parameters according to a plurality of sensing results obtained in one cycle period after the cycle period has expired, and send the updated pulse generation instruction to the pulse generator at the beginning of a next cycle period, which is not limited in this embodiment.

Figure 4:
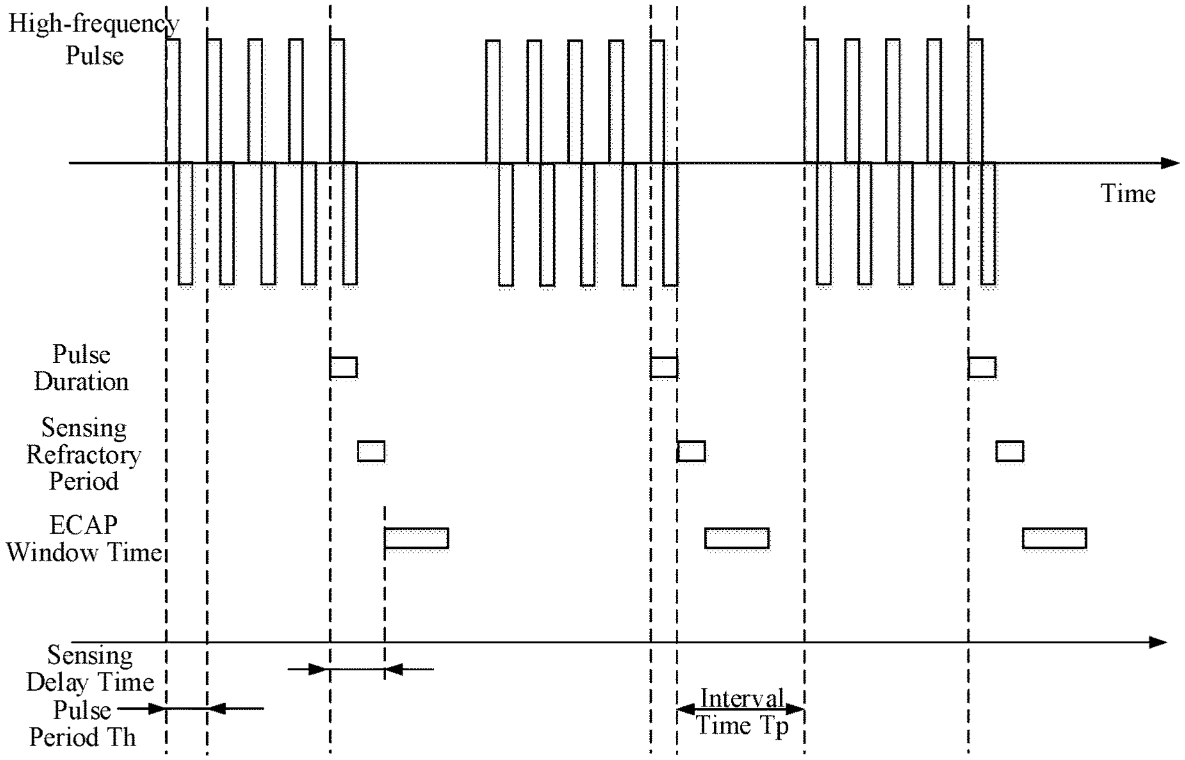
FIG. 4 is still another timing diagram of operating of a spinal cord stimulation device according to an embodiment of the present disclosure.

A pulse generation mode of the neural stimulation device in this embodiment includes a tonic spiking mode (also referred to as a forced discharge mode), and a tonic bursting mode. In the tonic spiking mode, the neural stimulation controller controls the pulse generator to generate a pulse at a pulse generation frequency below 150 Hz, and controls the ECAP sensor to turn on and subsequently sense the evoked compound action potential according to the above description. In the tonic bursting mode, the neural stimulation controller controls the pulse generator to generate a cluster of high-frequency pulses (the pulse generation frequency is in a range of 400 Hz to 600 Hz, such as 500 Hz and a corresponding pulse generation period Th is 2 ms), each cluster of high-frequency pulses including 4 to 6 pulses, the generation of the high-frequency pulses is paused within a certain interval time Tp (the interval time Tp is greater than 6.67 ms, for example, the interval time Tp is 20 ms, i.e., the frequency of generating each cluster of high-frequency pulses is less than 150 Hz), then the generation of the high-frequency pulses is continued, and so on. At this time, as shown in FIG. 4, when the neural stimulation controller generates a cluster of high-frequency pulses, the ECAP sensor is not turned on to sense the evoked compound action potential. When the last pulse in the cluster of high-frequency pulses is generated, the neural stimulation controller instructs the ECAP sensor to turn on while instructing the pulse generator to generate the pulse. Similar to that described above, the neural stimulation controller instructs the ECAP sensor to turn on, instructs the ECAP sensor to sense the evoked compound action potential after the elapsing of the sensing delay time, and instructs the ECAP sensor to turn off after instructing the ECAP sensor to sense the evoked compound action potential and the elapsing of the ECAP window time. The total duration of the pulse, obviously, refers to a total duration of the last pulse in a cluster of high-frequency pulses.

Figure 5:
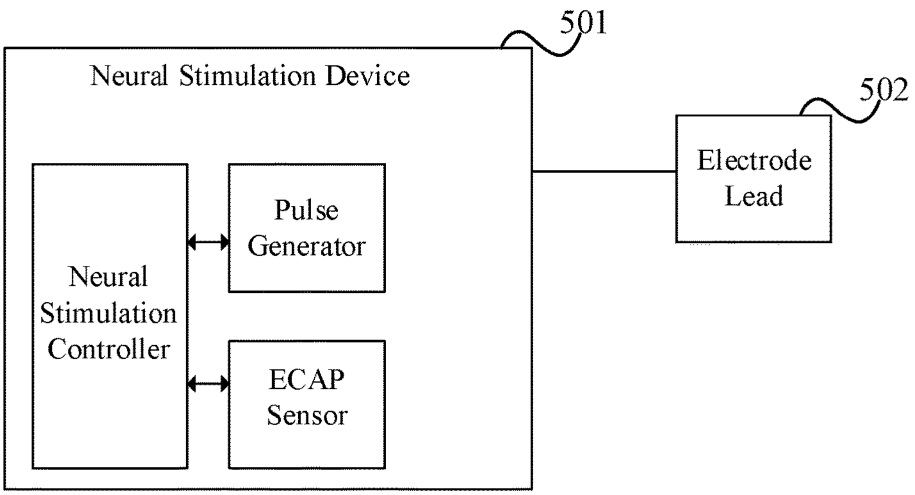
FIG. 5 is a schematic structural diagram of a neural stimulation system according to another embodiment of the present disclosure.

Another aspect of the embodiments of the present disclosure provides a neural stimulation system, as shown in FIG. 5, including the neural stimulation device 501 as described above and an electrode lead 502 electrically connected to the neural stimulation device. The electrode lead includes a plurality of stimulation electrodes and sensing electrodes, the stimulation electrodes are configured to transmit pulses into a body of a user, and the sensing electrodes are configured to transmit an evoked compound action potential caused by pulses to the ECAP sensor. The stimulation electrodes may be ring electrodes or segmented electrodes, etc. In this embodiment, a type of the electrodes is not specifically limited, for example, the electrode lead is an electrode lead provided with a ring electrode at distal end. For another example, the electrode lead is an electrode lead provided with a segmented electrode at a distal end. For still another example, the electrode lead is an electrode lead provided with a ring electrode and a segmented electrode at a distal end.

A control method applied at a neural stimulation device including a neural stimulation controller, a pulse generator and a ECAP sensor according to another aspect of the embodiments of the present disclosure includes the following operations.

The neural stimulation controller instructs the ECAP sensor to turn on while instructing the pulse generator to generate a pulse.

The neural stimulation controller instructs the ECAP sensor to sense an evoked compound action potential after instructing the pulse generator to generate the pulse and elapsing of a sensing delay time. The sensing delay time is the greater of a total duration of the pulse and a predetermined time.

The neural stimulation controller instructs the ECAP sensor to turn off after instructing the ECAP sensor to sense the evoked compound action potential and elapsing of an ECAP window time.

It is not difficult to find that this embodiment is a method embodiment corresponding to the device embodiment, and this embodiment may be implemented in cooperation with the device embodiment. The related technical details mentioned in the device embodiment are still effective in this embodiment, and are not repeated here in order to reduce repetition. Accordingly, the related technical details mentioned in this embodiment may also be applied to the device embodiment.

Figure 6:
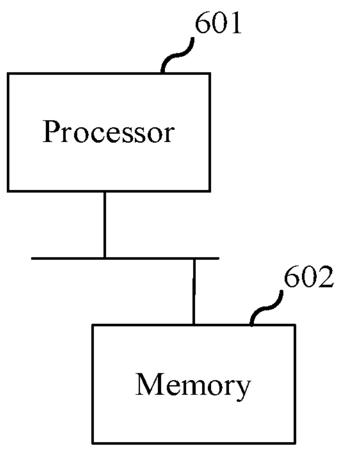
FIG. 6 is a schematic structural diagram of an electronic device according to another embodiment of the present disclosure.

Another aspect of the embodiments of the present disclosure further provides an electronic device, as shown in FIG. 6, including at least one processor 601 and a memory 602 communicatively connected to the at least one processor 601. The memory 602 stores instructions executable by the at least one processor 601, and the instructions, when executed by the at least one processor 601, cause the at least one processor 601 to perform a control method applied at a neural stimulation device. The method includes: instructing the ECAP sensor to turn on while instructing to generate a pulse; instructing to sense an evoked compound action potential after instructing to generate the pulse and elapsing of a sensing delay time, where the sensing delay time is the greater of a total duration of the pulse and a predetermined time; and instructing the ECAP sensor to turn off after instructing the ECAP sensor to sense the evoked compound action potential and elapsing of an ECAP window time.

The memory 602 and the at least one processor 601 are connected using a bus, the bus may include any number of interconnected buses and bridges, and the bus connects various circuits of the at least one processor 601 and the memory 602 together. The bus may also connect together various other circuits, such as a peripheral device, a voltage regulator, and a power management circuit, etc., which are well known in the art, and therefore are not further described herein. A bus interface provides an interface between the bus and a transceiver. The transceiver may be an element, or may be a plurality of elements, such as a plurality of receivers and transmitters, providing units for communicating with various other devices on a transmission medium. The data processed by the at least one processor 601 is transmitted on a wireless medium through an antenna, and further, the antenna receives the data and transmits the data to the at least one processor 601.

The at least one processor 601 is responsible for managing buses and general processing, and may also provide various functions including timing, peripheral interface, voltage regulation, power management, and other control functions. The memory 602 may be configured to store data used by the at least one processor 601 when performing operations.

Another aspect of the embodiments of the present disclosure further provides a non-transitory computer-readable storage medium storing a computer program. The non-transitory computer program, when executed by a processor, causes the processor perform a control method applied at a neural stimulation device including a neural stimulation controller, a pulse generator and a ECAP sensor. The control method includes: the neural stimulation controller instructing the ECAP sensor to turn on while instructing the pulse generator to generate a pulse; the neural stimulation controller instructing the ECAP sensor to sense an evoked compound action potential after instructing the pulse generator to generate the pulse and elapsing of a sensing delay time, where the sensing delay time is the greater of a total duration of the pulse and a predetermined time; and the neural stimulation controller instructing the ECAP sensor to turn off after instructing the ECAP sensor to sense the evoked compound action potential and elapsing of an ECAP window time.

That is, a person skilled in the art may understand that all or some of operations in the method in the above embodiments may be completed by a program instructing related hardware, and the program is stored in a storage medium and includes several instructions for enabling a device (which may be a single-chip microcomputer, a chip, etc.) or a processor to perform all or some of the operations in the method described in the embodiments of the present disclosure. The above storage medium includes various media that can store program codes, such as a USB flash disk, a mobile hard disk, a read-only memory (ROM), a random access memory (RAM), a magnetic disk, or an optical disc, etc.

It should be understood by those of ordinary skill in the art that the above embodiments are specific embodiments for implementing the present disclosure, and in practical applications, various changes may be made in form and detail without departing from the spirit and scope of the present disclosure.

What is claimed is:

1. A neural stimulation device, comprising: a neural stimulation controller, a pulse generator, and an evoked compound action potential (ECAP) sensor; wherein the neural stimulation controller is configured to:

instruct the ECAP sensor to turn on while instructing the pulse generator to generate a pulse;

instruct the ECAP sensor to sense an evoked compound action potential after a sensing delay time has elapsed since instructing the pulse generator to generate the pulse; and instruct the ECAP sensor to turn off after an ECAP window time has elapsed since instructing the ECAP sensor to sense the evoked compound action potential;

wherein the sensing delay time is determined based on whether a total duration of the pulse is greater than a predetermined time.

2. The neural stimulation device according to claim 1, wherein the neural stimulation controller is further configured to, before instructing the ECAP sensor to be activated, determine whether the ECAP sensor performs sensing the evoked compound action potential, and in response to the ECAP sensor performing sensing, instruct the ECAP sensor to be activated to perform sensing the evoked compound action potential.

3. The neural stimulation device according to claim 2, wherein the neural stimulation controller is configured to control whether the ECAP sensor performs sensing the evoked compound action potential by:

obtaining an accumulated duration of one or more pulse generation periods in which the evoked compound action potential has been sensed in a current cycle period; and controlling whether the ECAP sensor to perform sensing the evoked compound action potential in response to the accumulated duration being less than a first duration that is predetermined;

wherein the current cycle period includes at least two pulse generation periods.

4. The neural stimulation device according to claim 3, wherein the neural stimulation device further includes a human body posture sensor; and wherein:

the human body posture sensor is configured to sense a real-time posture of a human body; and the neural stimulation controller is further configured to communicate with the human body posture sensor to obtain a human body posture, restart a new cycle period in response to detecting that the human body posture changes within the current cycle period, and reset the accumulated duration to zero.

5. The neural stimulation device according to claim 3, wherein the neural stimulation device includes a first timer, a fourth timer, and a fifth timer; wherein:

the first timer is configured to be in a first timing mode having a first timing duration, wherein the first timing duration is a duration of the pulse generation periods;

the fourth timer is configured to be in a fourth timing mode having a fourth timing duration, wherein the fourth timing duration is a duration of the current cycle period; and the fifth timer is configured to be in a fifth timing mode having a fifth timing duration, wherein the fifth timing duration is equal to the first duration; and wherein the neural stimulation controller instructs the ECAP sensor to turn on in response to (i) the fourth timer and the fifth timer not having expired, and (ii) the first timer having expired.

6. The neural stimulation device according to claim 1, wherein the neural stimulation controller is further configured to update a parameter of the pulse according to the evoked compound action potential that is sensed.

7. The neural stimulation device according to claim 1, wherein the neural stimulation device is applied to spinal cord stimulation, dorsal root ganglion stimulation, sympathetic nerve stimulation, vagus nerve stimulation or deep brain stimulation.

8. The neural stimulation device according to claim 1, wherein the neural stimulation device includes a first timer, a second timer, and a third timer; and wherein:

the first timer is configured to be in a first timing mode having a first timing duration, wherein the first timing duration is a duration of a pulse generation period, and the neural stimulation controller instructs the ECAP sensor to turn on in response to the first timer being expired;

the second timer is configured to be in a second timing mode having a second timing duration in response to the neural stimulation controller instructing the ECAP sensor to turn on, wherein the second timing duration is a duration of the sensing delay time, and the neural stimulation controller instructs the ECAP sensor to sense the evoked compound action potential in response to the second timer being expired; and the third timer is configured to be in a third timing mode having a third timing duration in response to the neural stimulation controller instructing the ECAP sensor to sense the evoked compound action potential, wherein the third timing duration is a duration of the ECAP window time, and the neural stimulation controller instructs the ECAP sensor to turn off in response to the third timer being expired.

9. The neural stimulation device according to claim 1, wherein the neural stimulation device has a pulse generation mode, and the pulse generation mode includes a tonic spiking mode.

10. The neural stimulation device according to claim 1, wherein the neural stimulation device has a pulse generation mode, the pulse generation mode includes an excitation cluster generation mode, and the neural stimulation controller instructs the pulse generator to generate a last pulse in a cluster of high-frequency pulses while instructing the ECAP sensor to turn on.

11. A neural stimulation system, comprising: a neural stimulation device and an electrode lead electrically connected to the neural stimulation device; wherein the neural stimulation device includes a neural stimulation controller, a pulse generator, and an evoked compound action potential (ECAP) sensor; and wherein the neural stimulation controller is configured to:

instruct the ECAP sensor to turn on while instructing the pulse generator to generate a pulse;

instruct the ECAP sensor to sense an evoked compound action potential after a sensing delay time has elapsed since instructing the pulse generator to generate the pulse; and instruct the ECAP sensor to turn off after an ECAP window time has elapsed since instructing the ECAP sensor to sense the evoked compound action potential;

wherein the sensing delay time is determined based on whether a total duration of the pulse is greater than a predetermined time.

12. The neural stimulation system according to claim 11, wherein the neural stimulation controller is further configured to, before instructing the ECAP sensor to be activated, determine whether the ECAP sensor performs sensing the evoked compound action potential, and in response to the ECAP sensor performing sensing, instruct the ECAP sensor to be activated to perform sensing the evoked compound action potential.

13. The neural stimulation system according to claim 12, wherein the neural stimulation controller configured to control whether the ECAP sensor performs sensing the evoked compound action potential by:

obtaining an accumulated duration of one or more pulse generation periods in which the evoked compound action potential has been sensed in a current cycle period; and controlling whether the ECAP sensor to perform sensing the evoked compound action potential in response to the accumulated duration being less than a first duration that is predetermined;

wherein the current cycle period includes at least two pulse generation periods.

14. The neural stimulation system according to claim 13, wherein the neural stimulation device further includes a human body posture sensor; and wherein:

the human body posture sensor is configured to sense a real-time posture of a human body; and the neural stimulation controller is further configured to communicate with the human body posture sensor to obtain a human body posture, restart a new cycle period in response to detecting that the human body posture changes within the current cycle period, and reset the accumulated duration to zero.

15. The neural stimulation system according to claim 11, wherein the neural stimulation controller is further configured to update a parameter of the pulse according to the evoked compound action potential that is sensed.

16. The neural stimulation system according to claim 11, wherein the neural stimulation device has a pulse generation mode, and the pulse generation mode includes a tonic spiking mode.

17. The neural stimulation system according to claim 11, wherein the neural stimulation device has a pulse generation mode, the pulse generation mode includes an excitation cluster generation mode, and the neural stimulation controller instructs the pulse generator to generate a last pulse in a cluster of high-frequency pulses while instructing the ECAP sensor to turn on.

18. A control method, comprising:

applied at a neural stimulation device, wherein the neural stimulation device includes a neural stimulation controller, a pulse generator, and an evoked compound action potential (ECAP) sensor, and wherein the neural stimulation controller is configured to:

instruct the ECAP sensor to turn on while instructing the pulse generator to generate a pulse;

instruct the ECAP sensor to sense an evoked compound action potential after a sensing delay time has elapsed since instructing the pulse generator to generate the pulse; and instruct the ECAP sensor to turn off after an ECAP window time has elapsed since instructing the ECAP sensor to sense the evoked compound action potential;

wherein the sensing delay time is determined based on whether a total duration of the pulse is greater than a predetermined time.

* * * * *